United States Patent [19]

Ohlsson et al.

[11] Patent Number: 5,772,603

[45] Date of Patent: Jun. 30, 1998

[54] DEVICE FOR FILTERING ECG SIGNALS

[75] Inventors: Thomas Ohlsson, Hässelby; Peter Karlsson, Stockholm, both of Sweden

[73] Assignee: Siemens-Elema AB, Solna, Sweden

[21] Appl. No.: 867,959

[22] Filed: Jun. 3, 1997

Related U.S. Application Data

[63] Continuation of Ser. No. 276,257, Jul. 18, 1994, abandoned.

[30] Foreign Application Priority Data

Jul. 16, 1993 [SE] Sweden .................................. 9302432

[51] Int. Cl.[6] .................................................. A61B 5/0428
[52] U.S. Cl. .............................................................. 600/509
[58] Field of Search .................................. 128/696, 901; 600/503, 509

[56] References Cited

U.S. PATENT DOCUMENTS

| 3,580,243 | 5/1971 | Johnson ................................. 128/696 |
| 5,297,557 | 3/1994 | Reichl ..................................... 128/707 |
| 5,318,036 | 6/1994 | Arand et al. ............................. 128/901 |
| 5,333,616 | 8/1994 | Mills et al. ............................... 128/696 |
| 5,406,955 | 4/1995 | Bledsoe et al. .......................... 128/111 |
| 5,411,029 | 5/1995 | Hirei ........................................ 128/696 |

*Primary Examiner*—William E. Kamm
*Assistant Examiner*—George R. Evanisko
*Attorney, Agent, or Firm*—Hill & Simpson

[57] ABSTRACT

A device for filtering ECG signals has an A/D converter and a filter unit connected to the converter's output. The filter unit includes a filter, or a combination of filters with a non-linear phase response such that signals with frequencies in the passband of the filter, or the combination of filters, are delayed more than signals with frequencies in the transition band between the passband and the suppressed frequency band of the filter, or the combination of filters. A method for producing an FIR filter, with a phase response opposite to the phase response of a filter for filtering out DC components, or an IIR filter, suitable for use in the above-described device, is also disclosed in which the impulse response from the filter for filtering out DC components and low-frequency components or the IIR filter is reversed in time and sampled. The sampled values are then used for determining coefficients for the FIR filter.

11 Claims, 2 Drawing Sheets

DEVICE FOR FILTERING ECG SIGNALS

This is a continuation of application Ser. No. 08/276,257, filed Jul. 18, 1994 now abandoned.

BACKGROUND OF THE INVENTION

1. Field of the Invention

The present invention relates to a device for filtering ECG signals, of the type having an A/D converter for converting analog input signals to a series of digital values, corresponding to the input signals at different times, and a filter unit connected to the output of the A/D converter, and to a method for producing an FIR (finite duration impulse response) filter with a phase response opposite to the phase response of a filter for filtering out DC and low-frequency signal components or an IIR (infinite duration impulse response) filter.

2. Description of the Prior Art

The ECG signal recorded between two electrodes on the patient's body, e.g. on the arms and legs, also contains a DC potential, in addition to the ECG signal, which may be much larger than the ECG signal. These DC potentials or low-frequency signals vary because of relative movements of the body and the electrode as a result of, e.g., the patient's breathing movements.

Filtration of the signals is thus required for analysis of ECG signals.

Two-pass filtering is one way to remove these DC signals and low-frequency signals from the ECG signal. For this purpose, a filter with a linear phase is achieved by both forward and backward filtration of the signal with a filter with a non-linear phase, see, e.g., British Specification 1 556 512, which describes this filtration with analog filters. A linear phase is desirable at the filtration, since phase distortion is then eliminated and thus only a minor distortion of the ECG signal's morphology results. This method in which the signal must be fed to the filter both in the forward and in the backward (reverse) directions, however, cannot be used continuously, which is a major disadvantage when on-line filtering is desired in an ECG examination lasting a longer time.

The presence of high-frequency signals with small amplitudes on the microvolt level at the end of the QRS complex in post-infarction patients has been shown to be a good indication of an increased risk of future life-threatening ventricular arrhythmias, see European Heart Journal (1991), 12, pp. 473–480. High-pass filtration is needed in order to identify and analyze these late potentials. One problem in doing so is the ringing which is induced by the QRS signal itself and which readily drowns out any late potentials. Several proposals to solve this problem have been presented. In Link and Trahms, "Highpass Filters for Detecting Late Potentials", Proc. Computers in Cardiology 1992, pp. 159–162, the use of a non-recursive, monotone, binomial highpass filter for detecting late potentials is proposed.

U.S. Pat. No. 4,422,459 discloses a technique for identifying the presence or absence of a time segment containing high-frequency signals in the latter part of a patient's QRS complex and for measuring the magnitude of this segment. The measured analog ECG signals are then converted into digital signals, and normal QRS signals are averaged over some hundred beats in order to obtain a relatively noise-free complex. The latter part of the average values of the signals is then subjected to backward high-pass filtration so the ringings, which would otherwise occur after the QRS complex, are avoided. The disadvantage of this technique is the complexity of backward filtering.

U.S. Pat. No. 4,458,691 discloses a system for high-pass forward filtration of ECG signals for detection of late potentials, wherein an adaptive high-pass filter for selective filtration of different segments of the QRS complex is used to solve the problem of ringing. This technique also has several disadvantages. Ringing is not completely eliminated, and to reduce the ringing effect as much as possible short FIR filters with a linear phase are used, yielding poorer frequency splitting.

U.S. Pat. No. 4,458,692 discloses another method for detecting late potential by forward filtration of the ECG signal. Regulation of the filter gain dependent on the magnitude of the input signal is employed in an effort to solve the problem of ringing. The signal controlling the gain can be the output signal from a filter using the QRS signal as an input signal, and the influence, e.g, the R spike on the output signal, and thus on the ringing arising after the R spike, can be limited if the gain in the filter is limited when the input signal rises above a defined level. This method also has the disadvantage of failing to eliminate all ringings, and a steep filter slope must be sacrificed.

U.S. Pat. No. 4,492,235 also relates to detection of late potentials by forward filtration of the QRS signal; an adaptive high-pass filtration being employed to overcome the problem of ringing.

U.S. Pat. No. 5,025,794 discloses a further method for forward filtration of late potentials in which sampled values of the QRS signal are subjected to both forward and backward filtration, wherein the filtered signals are added and the summation signal is smoothed to yield signal components corresponding to the late potentials. The method described in this patent is complicated.

SUMMARY OF THE INVENTION

An object of the present invention is to provide a device for the filtration of ECG signals in which the above-described disadvantages of the prior art are avoided.

The above object is achieved in accordance with the principles of the present invention in a device for filtering EGG signals wherein a filter unit is connected to an output of an analog-to-digital converter, to which the measured EGG signals are supplied. The filter unit may be formed by a single filter or by a combination of filters. The filter unit has a non-linear phase response such that signals having frequencies in the passband of the filter or the combination of filters are delayed more than signals with frequencies in the transition band between the passband and the suppressed frequency band of the filter or the combination of filters.

In a device according to the invention, the filter thus has a non-linear phase response with "abnormal" phase properties. A normal high-pass filter with a non-linear phase response delays the signal in the transition band, between the suppressed frequency band and the pass band, more than the signal in the high-frequency passband. The filter in the device according to the invention is devised, however, so the signal in the passband is delayed more than the signal in the transition band, which has proved to be surprisingly advantageous for the applications in question.

In the device according to the invention, the filtration can also be performed in a combination of filters with the above mentioned characteristic. With the device according to the invention, baseline filtration and detection of late potentials inter alia, are thus possible in a simple manner by forward filtration of the ECG signal. The filtration device can also be advantageously used for form classification of the ECG complex, ST measurements and delimitation of the ECG complex.

According to advantageous refinements of the device according to the invention, a filter, such as an RC circuit, is disposed before the A/D converter to filter out DC and low-frequency components in the ECG signal, and the filter unit has a filter characteristic molded on an asymmetrical FIR filter with a phase response opposite to the phase response of said filter for filtering out DC and low-frequency components. If the baseline filtration is performed with a filter with a linear phase, the lower cut-off frequency can be chosen very close to the repetition frequency of the QRS complex, i.e. the heart's pulse rate. Because of phase distortion in an AC circuit, the cut-off frequency must be about tenfold lower to prevent excessive measurement errors. With the device according to the invention, therefore, suppression of the low-frequency fault signals, arising when a patient moves during, e.g., an exercise ECG, can be greatly improved by a tenfold increase of the cut-off frequency of the high-pass filter. Conventional backward filtration is not possible when conducting ECG recording during an exercise test lasts for about 15 minutes.

Another object of the present invention is to propose a method of the type initially described for producing a filter unit with an FIR filter characteristic suitable for use in the device according to the invention.

This object of the invention is achieved in a method for producing a filter unit with an FIR filter characteristic having a phase response which is opposite to the phase response of a filter for filtering out d.c. and low-frequency signal components, or which is opposite to an IIR filter. In accordance with the method, the impulse response of a filter, with respect to which the aforementioned FIR filter characteristic is to have the aforementioned opposite phase response, is reversed in time and is sampled. The sampled values are then used for determining coefficients for the FIR filter. A filter unit with an FIR filter characteristic produced in accordance with this method is suitable for use in the above-described device for filtering ECG signals.

With the method according to the invention, it is thus possible to construct a filter unit with an FIR filter characteristic whose output in the forward filtration is virtually identical to the output signal from, e.g., a corresponding IIR filter characteristic in backward filtration. Conventional thinking would hold that the use of such an FIR filter would require unacceptably extensive calculations, however, the inventors have found that the calculations surprisingly do not have to be performed with very great precision, so the analysis time is not prolonged by the calculations.

DESCRIPTION OF THE PREFERRED EMBODIMENTS

Figure 1:
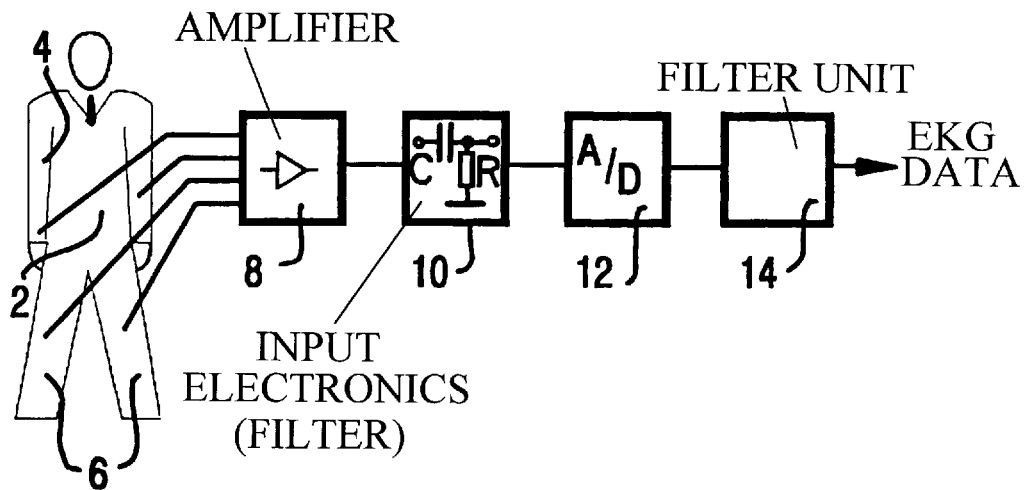
FIG. 1 shows equipment for recording ECG signal with the device according to the invention.

An ECG is measured as the potential between electrodes on the body of a patient 2, e.g., on her/his arms 4 and legs 6, as schematically shown in FIG. 1. The measured signals are supplied to an amplifier 8.

Figure 2:
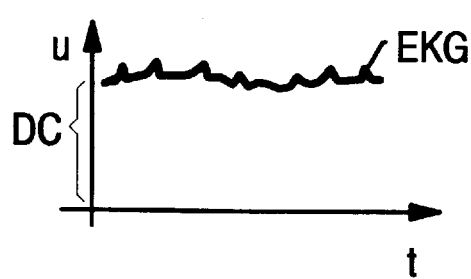
FIG. 2 shows an example of a recorded ECG signal with a large superimposed DC component.

The difference in the potential measured between two electrodes on the patient 2 contains a DC potential, in addition to the ECG signal, which may be much larger than the ECG signal itself, as shown in FIG. 2, which shows the unprocessed ECG signal as recorded. The ECG signal itself consists of minor variations on a large voltage. This large DC voltage also varies with the movements of the body and the electrodes, so elimination of this voltage from the recorded signal is desirable.

Figure 3:
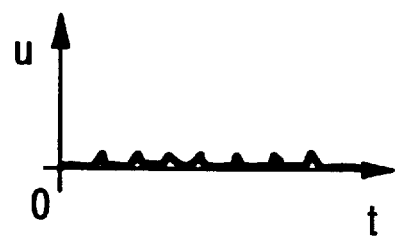
FIG. 3 shows the ECG signal in FIG. 2 with the DC component filtered out by the device of the invention.

One way of achieving this is to provide the input electronics 10 of the A/D converter 12 with a time constant, i.e., to AC couple the amplifier 8 thereto. With an RC coupling, the DC component in the recorded signal is therefore filtered out, of FIG. 3, and the ECG can be measured around the zero line. A recording window can thus be placed around the zero line. The dynamic area will then be much smaller, and resolution requirements for the A/D conversion are reduced from 17 bits to 12 bits.

Such filtration, because of its associated non-linear phase shift, has major disadvantages for the subsequent processing of the ECG signal. The inventors have perceived that the signal distortion depends mainly on the fact that the signal in the suppression frequency band is delayed more than the signal in the passband. A major improvement would be achieved if the filtration could be performed with a linear phase, all signal frequencies then being delayed to an equal degree.

In accordance with the invention, the signals are therefore filtered in an additional filter unit 14 which has the same phase response as the RC circuit but with an opposite sign.

Such a filter 14 can be appropriately realized in the form of a digital filter unit, so that the analog measurement signals are converted in the A/D converter 12 into a series of digital values, corresponding to the signal value at periodic times and supplied to the filter unit 14.

Figure 5:
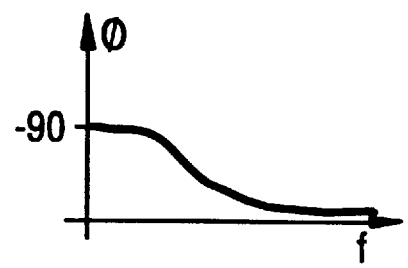
FIGS. 4 and 5, respectively, show the amplitude characteristic and the phase characteristic of a high-pass filter in which the signal in the suppressed frequency band is delayed more than signal in the passband in accordance with the invention.
Figure 4:
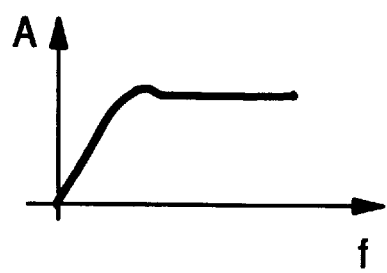

The amplitude and phase characteristics of the RC circuit are illustrated in FIGS. 4 and 5.

Figure 6:
FIG. 6 shows the impulse response for a filter.
Figure 7:
FIG. 7 illustrates the sampling of this impulse response, reversed in time, for determining the coefficients for a FIR filter with the desired characteristic in accordance with the invention.

The impulse response of the RC circuit is the starting point in constructing a filter unit 14 which delays the signal in the passband more than the signal in the suppressed frequency band according to the above, see FIG. 6. The impulse response is reversed in time and sampled, and the sampled values are then employed as coefficients for an asymmetrical FIR filter. This is illustrated in FIG. 7 in which each sampled value forming a coefficient for the FIR filter characteristic for the filter unit 14 has been marked with an x.

The RC filter for filtering out DC and low-frequency components is a hardware filter for which the filter unit 14 subsequently shall compensate. The filter unit then shall have the same amplitude characteristic as the hardware filter, whereas its phase characteristic shall be the same, although with the opposite sign.

Figure 1A:
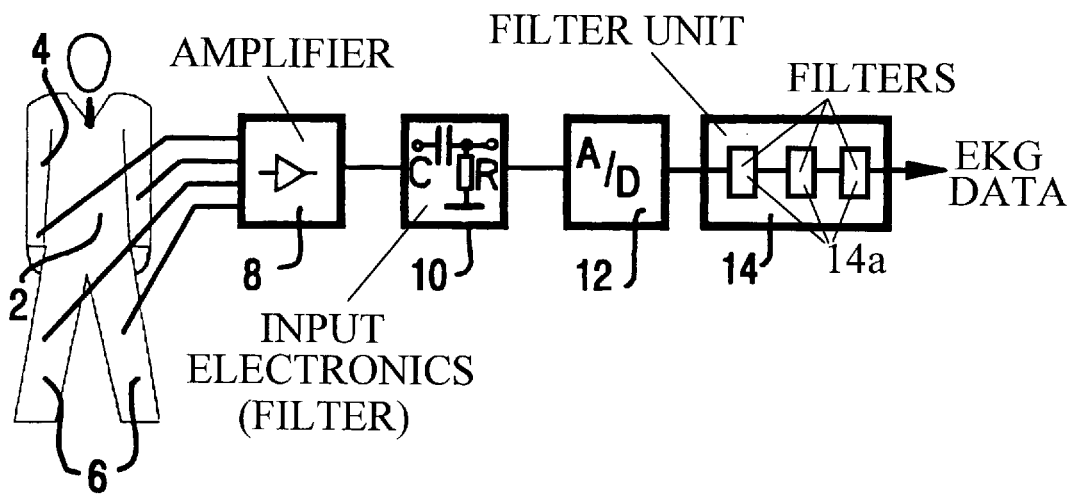
FIG. 1a shows a variation of the equipment of FIG. 1 wherein the filter unit is composed of a number of filters.

As shown in FIG. 1a filter unit 14 can also be realized as a combination of filters 14a, the combination of filters 14a then having the aforementioned characteristic for the overall filter unit 14.

After the ECG signal has been filtered in this filter unit 14, all signal frequencies will be delayed to about the same degree and the signal is suitable for continued processing.

The amplitude characteristic for the combined filtration corresponds to the characteristic of a cascade coupling of both the filter 10 and the filter unit 14, and the result of the combined filtration corresponds to the result which would be achieved if forward and backward filtration were performed with the RC-circuit. With the device shown in FIG. 1, two-pass filtering is thus realized without any need for backward filtration of the signal with the disadvantages such a method would entail, as discussed above.

If baseline filtering is performed with a filter with a linear phase, the lower cut-off frequency can be chosen very close to the repetition frequency of the QRS complex, i.e. close to the heart's pulse rate. As a result of phase distortion in an RC circuit, the cut-off frequency must be set ten times lower to prevent excessively large measurement errors. With the above-described device according to the invention, the suppression of the low-frequency fault signals arising when a patient moves, e.g. during an exercise ECG, can be greatly improved by increasing the cut-off frequency for the high-pass filter tenfold. Conventional backward filtration would not be possible under these circumstances because an ECG is recorded during an exercise test lasting about 15 minutes.

One embodiment of the device according to the invention was described above for baseline filtration, however, the device according to the invention is suitable for a plurality of other applications.

A device of the above-described kind is thus also very suitable for the detection of late potentials without any need for backward filtration in order to overcome the problem of ringing. The first part of the QRS complex is for this purpose first filtered in an IIR filter, whereupon the latter part of the complex and the signal for a defined period of time thereafter are filtered in an asymmetrical FIR filter constructed in a manner analogously to the construction of the above-described filter for baseline filtration, i.e. the impulse response from the IIR filter is reversed in time and sampled, and the sampled values are then employed as coefficients for the FIR filter.

The IIR filter's impulse response is infinite, which would therefore yield an infinite number of coefficients in the FIR filter. The impulse response normally subsides so rapidly, however, that a good approximation of the impulse response is achieved If the sequence of coefficients is cut off at a manageable, finite number.

With the device according to the invention, the problems of ringing and phase distortion are consequently eliminated at the filtration of ECG signals with no need to perform backward filtration of the signals or parts thereof.

The device according to the invention is also useful for form classification of ECG complexes, ST measurements of ECG complexes and delimitation of the ECG complex, as mentioned above.

ST measurements relate to measurements made in the interval between the S in the QRS complex and the T wave. Useful information can be found in this region, and it is well-known to obtain measurements in this interval. Baseline filtration is then especially critical in exercise tests. The ST interval is a "plateau," and thus correct reproduction of low frequencies is essential for this plateau to appear. As mentioned, forward-backward filtration has long been employed for baseline filtration, and this method has been common in conjunction with ST measurements. With the present invention, also this measurement is therefore greatly simplified.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device for filtering analog ECG signals for use with a source of said ECG signals comprising:

filter means, having inputs supplied with analog ECG signals, for filtering out components of said ECG signals, said filter means having an amplitude characteristic and a phase response, and producing filtered ECG signals:

an analog-to-digital converter, having inputs and to which said filtered ECG signals are supplied, and which converts said filtered ECG signals into an output signal consisting of a series of successive digital values corresponding to said filtered ECG signals at said inputs at successive times, said output signal exhibiting differing frequency contents at different times; and high-pass filter means, to which said output signal from said analog-to-digital converter is supplied for forward filtration only, having an amplitude characteristic and a non-linear phase response with a frequency passband, a suppressed frequency band and a transition band between said passband and said suppressed frequency band, for delaying an output signal from said analog-to-digital converter with a frequency in said passband more than an output signal from said analog-to-digital converter with a frequency in said transition band, said amplitude characteristic of said high-pass filter means being the same as the amplitude characteristic of said filter means, and said phase response of said high-pass filter means being opposite to the phase response of said filter means.

2. The device as claimed in claim 1 wherein said filter means comprises a single filter.

3. The device as claimed in claim 1 wherein said filter means comprises a plurality of filters.

4. The device as claimed in claim 1 wherein said filter means comprises a high-pass filter.

5. The device as claimed in claim 1 wherein said ECG signals contain d.c. and low-frequency components and wherein said filter means comprises means for filtering out said d.c. and low-frequency components in said ECG signals.

6. The device as claimed in claim 5 wherein said filter which filters out d.c. and low-frequency components comprises a hardware filter disposed before said analog-to-digital converter.

7. The device as claimed in claim 6 wherein said filter comprises an RC circuit.

8. The device as claimed in claim 1 wherein said ECG signal includes a QRS pattern having a repetition frequency, and wherein said filter means comprises a high-pass filter having a cutoff frequency which is lower than said repetition frequency.

9. The device as claimed in claim 1 wherein said filter means comprises an asymmetrical high-pass FIR filter.

10. The device as claimed in claim 1 wherein said ECG signals include a QRS pattern, and wherein said analog-to-digital converter comprises converter means for converting a portion of said QRS pattern and a portion of said ECG signals following said QRS pattern into said digital values for identifying late potentials in said ECG signals.

11. The device as claimed in claim 10 wherein said ECG signals each contain a first portion in said QRS pattern preceding said late potentials and wherein said filter means comprises an IIR filter which filters out said first portion.

* * * * *